United States Patent [19]

Wannamaker et al.

[11] Patent Number: 5,350,758

[45] Date of Patent: Sep. 27, 1994

[54] PIPERIDYL SULFONAMIDES AND SULFOXAMIDES AS INHIBITORS OF CHOLESTEROL BIOSYNTHESIS

[75] Inventors: Marion W. Wannamaker, West Chester; William A. VanSickle, Cincinnati; William R. Moore, Fairfield, all of Ohio

[73] Assignee: Merrell Dow Pharmaceuticals Inc., Cincinnati, Ohio

[21] Appl. No.: 993,497

[22] Filed: Dec. 18, 1992

Related U.S. Application Data

[63] Continuation of Ser. No. 910,604, Jul. 8, 1992, abandoned.

[51] Int. Cl.$^5$ ............... C07D 211/96; A61K 31/445
[52] U.S. Cl. .................... 514/315; 514/317; 514/326; 514/327; 546/214; 546/216; 546/219; 546/242; 546/248
[58] Field of Search ............ 546/214, 216, 217, 226, 546/242, 245, 248, 219; 514/315, 317, 326, 327

[56] References Cited

U.S. PATENT DOCUMENTS

| | | | |
|---|---|---|---|
| 2,580,411 | 1/1952 | Cusic | 260/561 |
| 3,178,439 | 4/1965 | Cislak | 260/294.7 |
| 3,185,678 | 5/1966 | Abood | 260/239 |
| 4,316,903 | 2/1982 | Grier et al. | 424/267 |
| 4,326,067 | 4/1982 | Fazio | 548/347 |
| 4,565,819 | 1/1986 | Vincent et al. | 514/307 |
| 4,695,575 | 9/1987 | Janssens et al. | 514/322 |
| 4,812,451 | 3/1989 | Shanklin, Jr. et al. | 514/212 |
| 4,857,648 | 8/1989 | Broger et al. | 546/147 |
| 4,906,659 | 3/1990 | Harada et al. | 514/478 |
| 4,940,705 | 7/1990 | Boshagen et al. | 514/227.8 |
| 5,084,461 | 1/1992 | Wannamaker et al. | 514/307 |

FOREIGN PATENT DOCUMENTS

| | | |
|---|---|---|
| 0029618 | 6/1981 | European Pat. Off. . |
| 0235942 | 9/1987 | European Pat. Off. . |
| 0420116 | 4/1991 | European Pat. Off. . |
| 421441 | 4/1991 | European Pat. Off. ......... 546/242 |
| 0468434 | 1/1992 | European Pat. Off. . |
| 0468457 | 1/1992 | European Pat. Off. . |
| 471236 | 2/1992 | European Pat. Off. ......... 546/242 |
| 1145616 | 3/1963 | Fed. Rep. of Germany . |
| 3011504 | 2/1980 | Fed. Rep. of Germany . |
| 3433036 | 3/1986 | Fed. Rep. of Germany . |
| 1261160 | 2/1953 | France . |
| 2272643 | 12/1975 | France . |
| 3044573 | 4/1978 | Japan . |
| 0505251 | 2/1969 | Switzerland . |
| 1102357 | 2/1968 | United Kingdom . |
| 1415682 | 11/1975 | United Kingdom . |
| 1420758 | 1/1976 | United Kingdom . |

OTHER PUBLICATIONS

Ikeda et al., Heterocycles, 27(4), pp. 943–953 (1988).
Mercer, et al., Comp. Biochem. Physiol 80B(2):341–346 (1985).
Jeney, et al., Chemical Abstract 67(5):21035p (1967).
Beger, et al., Chemical Abstract 89(23):196901z (1978).
Mathison, et al., Chemical Abstracts 78(11):71860b (1973).
Matsuda, et al., Chemical Abstracts 109(7):50259f (1988).
Kameoka, et al., Chemical Abstracts 104(6)43107y (1986).
Chemical Abstracts 51(17):12907 (1957).
Barney, et al., Tetrahedron Letters 31(39):5547–5550 (1990).
Zeyyreu, et al., Chapter 6 "Kinetics III–Reversible Inhibition of Enzyme action" in The Study of Enzyme Mechanisms, A Wiley-Interscience Publication (1974).
Pike and Brown, "Nutrition:An Integrated Approach" J. Wiley & Sons, pp. 531–535 (1954).
Ferles, et al., Chemical Abstracts 79(23):136948d (1973).
Gerst, et al., Biochemical Pharmacology 37(10):1955–1964 (1988).

Primary Examiner—Marianne M. Cintins
Assistant Examiner—Phyllis G. Spivack
Attorney, Agent, or Firm—Charlotte L. Barney

[57] ABSTRACT

The present invention relates to piperidyl sulfonamides and sulfoxamides which are useful as inhibitors of cholesterol biosynthesis and as agents which lower total serum cholesterol in patients in need thereof.

7 Claims, No Drawings

PIPERIDYL SULFONAMIDES AND SULFOXAMIDES AS INHIBITORS OF CHOLESTEROL BIOSYNTHESIS

This is a continuation of application Ser. No. 07/910,604, filed Jul. 8, 1992 now abandoned.

BACKGROUND OF THE INVENTION

The present invention relates to certain novel piperidyl amides, sulfonamides and sulfoxamides which are useful as inhibitors of cholesterol biosynthesis and as agents which lower total serum cholesterol in patients in need thereof. The present invention also provides pharmaceutical compositions for the use of these novel compounds.

The conversion of the acyclic polyolefin squalene to the cyclic steroid lanosterol is a key step in the biogenesis of cholesterol. This conversion occurs in two steps. Squalene epoxidase catalyzes the conversion of squalene to (3S)-2,3-oxidosqualene. Oxidosqualene cyclase then converts (3S)-2,3-oxidosqualene to lanosterol. Lanosterol is converted through a number of subsequent enzymatic steps to cholesterol. Inhibition of squalene epoxidase decreases the amount of oxidosqualene available for conversion to cholesterol. Inhibition of oxidosqualene cyclase decreases the amount of lanosterol available for conversion to cholesterol. Inhibition of squalene epoxidase and/or oxidosqualene cyclase thus results in a decrease in the amount of cholesterol synthesized and ultimately causes a lowering of cholesterol in the blood.

Atherosclerosis, as manifested in its major clinical complication, ischemic heart disease, continues to be a major cause of death in industrialized countries. It is now well accepted that atherosclerosis can begin with local injury to the arterial endothelium followed by proliferation of arterial smooth muscle cells from the medial layer to the intimal layer along with deposition of lipid and accumulation of foam cells in the lesion. As the atherosclerotic plaque develops it progressively occludes more and more of the affected blood vessel and can eventually lead to ischemia or infarction. Therefore, it is desirable to provide methods of inhibiting the progression of atherosclerosis in patients in need thereof.

There is now a large body of evidence demonstrating that hypercholesterolemia is an important risk factor associated with heart disease. For example, in December 1984, a National Institute of Health Consensus Development Conference Panel concluded that lowering definitely elevated blood cholesterol levels (specifically blood levels of low-density lipoprotein cholesterol) will reduce the risk of heart attacks due to coronary heart disease. Accordingly, it is desirable to provide a method for reducing blood cholesterol in patients with hypercholesterolemia.

Typically, cholesterol is carried in the blood of warm-blooded animals in certain lipid-protein complexes such as chylomicrons, very low density lipoprotein (VLDL), low density lipoprotein (LDL), and high density lipoprotein (HDL). It is widely accepted that LDL functions in a way that directly results in deposition of the LDL cholesterol in the blood-vessel wall and that HDL functions in a way that results in the HDL picking up cholesterol from the vessel wall and transporting it to the liver where it is metabolized [Brown and Goldstein, Ann. Rev. Biochem. 52, 223 (1983); Miller, Ann. Rev. Med. 31, 97 (1980)]. For example, in various epidemiologic studies the LDL cholesterol levels correlate well with the risk of coronary heart disease whereas the HDL cholesterol levels are inversely associated with coronary heart disease [Patton et al., Clin. Chem. 29, 1890 (1983)]. It is generally accepted by those skilled in the art that reduction of abnormally high LDL cholesterol levels is effective therapy not only in the treatment of hypercholesterolemia but also in the treatment of atherosclerosis.

The novel piperidyl amides sulfonamides and sulfoxamides of the present invention are inhibitors of squalene epoxidase and/or oxidosqualene cyclase. These compounds thus inhibit cholesterol biosynthesis and are useful in lowering blood cholesterol in patients in need thereof.

SUMMARY OF THE INVENTION

The present invention relates to novel piperidyl amides of the formula (I) and novel piperidyl sulfonamides and piperidyl sulfoxamides of the formula (II)

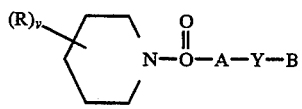

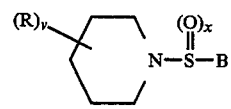

wherein

A is a $C_2$–$C_{14}$ alkylene;
Y is a methylene, oxygen or sulfur;
B is a $C_2$–$C_{14}$ alkylene,

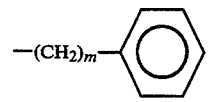

or

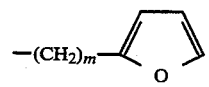

m is an integer 0 or 1;
x is an integer 1 or 2;
v is an integer 0, 1 or 2; and
R is -$(CH_2)_m$OH, with the proviso that when m is 0, R cannot be in the 2-position of the piperidine ring or a radical of the formula

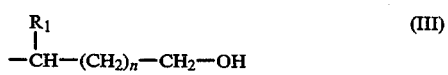

wherein n is an integer 0, 1, 2 or 3; and $R_1$ is hydrogen, phenyl, vinyl or a $C_1$–$C_4$ alkyl; provided that for piperidyl amides compounds of formula (I), when R is a radical of the formula

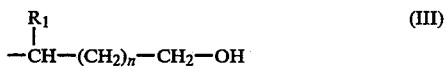

Y is not methylene.

The present invention further provides a method of inhibiting the biosynthesis of cholesterol in a patient in need thereof comprising administering to said patient an effective cholesterol biosynthesis inhibiting amount of a compound of formula (I) or formula (II).

The present invention also provides a method of lowering plasma cholesterol in a patient in need thereof, and a method of treating a patient afflicted with hypercholesterolemia, comprising administering to said patient an effective hypocholesterolemic amount of a compound of formula (I) or formula (II).

DETAILED DESCRIPTION OF THE INVENTION

As used herein the term "Y" refers to an oxygen atom, a sulfur atom or a methylene group. In other words, the term "Y" refers to a divalent radical of the formula -O-, -S- or -CH$_2$-. The term "halogen", or "halo" or "Hal" refers to a chlorine, bromine, or iodine atom.

As used herein the term "C$_2$-C$_{14}$ alkylene" refers to a saturated or unsaturated hydrocarbylene radical of from 2 to 14 carbon atoms of straight or branched chain configuration having 0 to 5 double bonds. Specifically included within the scope of the term are the radicals -CH$_2$CH$_2$-, -CH$_2$CH$_2$CH$_2$-, CH$_2$(CH$_2$)$_2$CH$_2$-, -CH$_2$(CH$_2$)$_3$CH$_2$-, -CH$_2$(CH$_2$)$_4$CH$_2$-, -CH$_2$(CH$_2$)$_5$CH$_2$-, -CH$_2$(CH$_2$)$_6$CH$_2$-, -CH$_2$(CH$_2$)$_7$CH$_2$-, -CH$_2$(CH$_2$)$_8$CH$_2$-, -CH$_2$(CH$_2$)$_9$CH$_2$-, -CH$_2$(CH$_2$)$_{10}$CH$_2$-, -CH$_2$(CH$_2$)$_{11}$CH$_2$-, -CH$_2$(CH$_2$)$_{12}$CH$_2$-, -CH(CH$_3$)CH$_2$-, -CH(CH$_3$)CH$_2$CH$_2$-, -CH(CH$_3$)CH$_2$CH$_2$CH$_2$-, -CH(CH$_3$)CH$_2$(CH$_2$)$_2$CH$_2$- , -CH(CH$_3$)CH$_2$CH(CH$_3$)-, -CH(CH$_3$)CH$_2$CH$_2$CH(CH$_3$)-, -CH(CH$_3$)CH$_2$(CH$_2$)$_2$CH(CH$_3$)-, -C(CH$_3$)-CH$_2$-(CH$_2$)$_2$-C(CH$_3$)=CH-(CH$_2$)$_2$-C(CH$_3$)=CH-(CH$_2$)$_2$-C(CH$_3$) =CH$_2$-, -CH(CH$_3$)-(CH$_2$)$_3$-CH(CH$_3$)-(CH$_2$)$_3$-CH(CH$_3$)-(CH$_2$)$_3$-CH(CH$_3$)-CH$_2$.

As used herein the term "C$_2$-C$_{14}$ alkyl" refers to a saturated or unsaturated hydrocarbyl radical of from 2 to 14 carbon atoms of straight or branched chain configuration having 0 to 5 double bonds. Specifically included within the scope of the term are the radicals -CH$_2$CH$_3$, -CH$_2$-CH$_2$CH$_3$, -CH$_2$(CH$_2$)$_2$CH$_3$, -CH$_2$(CH$_2$)$_3$CH$_3$, -CH$_2$(CH$_2$)$_4$CH$_3$, -CH$_2$(CH$_2$)$_5$CH$_3$, -CH2(CH$_2$)$_6$CH$_3$, -CH$_2$(CH$_2$)$_7$CH$_3$, -CH$_2$(CH$_2$)$_8$CH$_3$, -CH$_2$(CH$_2$)$_9$CH$_3$, -CH$_2$(CH$_2$)$_{10}$CH$_3$, -CH$_2$(CH$_2$)$_{11}$CH$_3$, -CH$_2$(CH$_2$)$_{12}$CH$_3$, -CH(CH$_3$)CH$_2$CH$_3$, -CH(CH$_3$)CH$_2$CH$_2$CH$_3$, -CH(CH$_3$)CH$_2$(CH$_2$)$_2$CH$_3$, -CH(CH$_3$)CH$_3$, -CH(CH$_3$)CH$_2$CH$_2$CH$_2$CH$_3$, -CH(CH$_3$)CH$_2$(CH$_2$)$_2$CH$_2$CH$_3$, -CH(CH$_3$)-CH$_2$-(CH$_2$)$_2$-C(CH$_3$)=CH-(CH$_2$)$_2$-C(CH$_3$)=CH-(CH$_2$)$_2$-C(CH$_3$)=CH$_2$, -CH(CH$_3$)-(CH$_2$)$_3$-CH(CH$_3$)-(CH$_2$)$_3$-CH(CH$_3$)-(CH$_2$)$_3$-CH(CH$_3$)-CH$_3$.

The compounds of formula (I) and formula (II) bear a piperidyl moiety which can be unsubstituted or substituted with one or two substituents selected from the group consisting of -(CH$_2$)$_m$OH or a radical of the formula -CH(R$_1$)-(CH$_2$)$_n$-CH$_2$OH, wherein n is an integer 0, 1, 2 or 3; and R$_1$ is hydrogen, phenyl, vinyl or a C$_1$-C$_4$ alkyl. As used herein the term "C$_1$-C$_4$ alkyl" refers to a saturated hydrocarbyl radical of from 1 to 4 carbon atoms of straight or branched chain configuration, including methyl, ethyl, n-propyl, isopropyl, n-butyl, isobutyl and t-butyl. The piperidyl moiety may bear substituents in any of the 2, 3, 4, 5 or 6 positions. In those instances wherein the piperidyl ring of the compound of formula (I) or formula (II) bears two substituents, the two substituents may be attached at the same or at different carbon atoms in the piperidyl ring. More particularly, the following piperidyl moieties are specifically contemplated as being included within the scope of formula (1): 1-piperidyl, 4-hydroxypiperidyl, 3-hydroxypiperidyl and 3,4-dihydroxypiperidyl.

The compounds of Formula (I) wherein Y is sulfur or oxygen can be prepared by utilizing procedures and techniques well known and appreciated by one of ordinary skill in the art. A general synthetic scheme for preparing these compounds is set forth in Scheme A wherein all substituents, unless otherwise indicated, are previously defined.

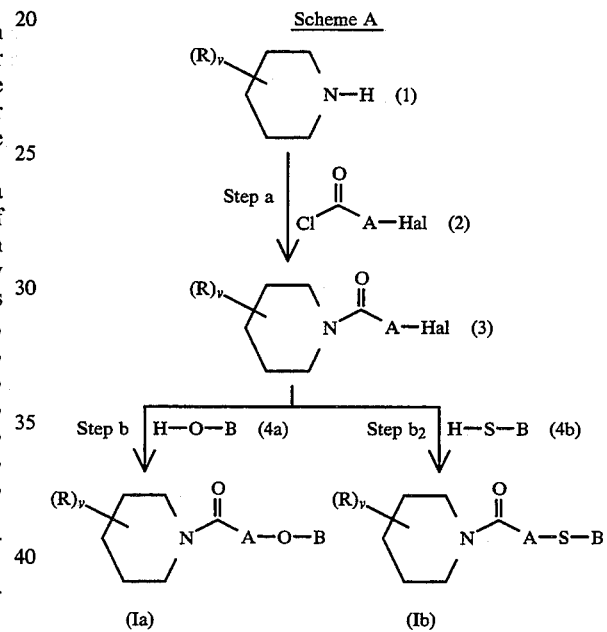

Scheme A

Scheme A provides a general synthetic scheme for preparing compounds of Formula (I) wherein Y is oxygen or sulfur.

In step a, the appropriate 1-(λ-halo-l-oxoalkyl)piperidine compound of structure (3) can be prepared by an amination reaction. For example, an appropriate piperidine compound of structure (1) can be reacted with the appropriate λ-halo-acetyl chloride of structure (2) in the presence of a suitable non-nucleophilic base such as triethylamine. The reactants are typically contacted in a suitable aprotic solvent, such as methylene chloride. For those piperidine compounds of structure (1) wherein R is -(CH$_2$) $_m$OH or a radical of the formula -CH(R$_1$)-(CH$_2$)$_n$-CH$_2$OH, the hydroxy functionality is protected prior to the amination reaction of step a. The selection and utilization of suitable protecting groups is well known by one or ordinary skill in the art and is described in "*Protective Groups in Organic Syntheses*", Theodora W. Greene, Wiley (1981).

In step b, the appropriate compound of Formula (I) wherein Y is oxygen or sulfur can be prepared by an alkylation reaction. For example, in step b$_1$, an appropriate 1-(λ-halo-l-oxoalkyl)-piperidine of structure (3) can be reacted with an alcohol of structure (4a) in the presence of a suitable non-nucleophilic base, such as potassium carbonate, sodium hydride or 1,8-diazabicyclo[5.4.0]undec-7-ene (DBU) to give the corresponding compound of Formula (Ia) wherein Y is oxygen. Similarly, in step b2, an appropriate 1-(λ-halo-l-oxoalkyl)-piperidine compound of structure (3) can be reacted with a mercaptan of structure (4b) to give the corresponding compound of Formula (Ib) wherein Y is sulfur. For those piperidine compounds of formula (Ia) or formula (Ib) wherein R is -(CH$_2$)$_m$OH or a radical of the formula -CH(R$_1$)-(CH$_2$)$_n$-CH$_2$OH, the protecting group on the hydroxy functionality is removed to give the appropriate piperidine compounds of formula (Ia) or formula (Ib) wherein R is -(CH$_2$)$_m$OH or a radical of the formula -CH(R$_1$)-(CH$_2$)$_n$-CH$_2$OH. The selection and utilization of suitable protecting groups is well known by one or ordinary skill in the art and is described in "*Protective Groups in Organic Syntheses*", Theodora W. Greene, Wiley (1981).

Starting materials for use in the general synthetic procedures outlined in Scheme A are readily available to one of ordinary skill in the art.

The following examples present typical syntheses as described in Scheme A. These examples are understood to be illustrative only and are not intended to limit the scope of the present invention in any way. As used herein, the following terms have the indicated meanings: "g" refers to grams; "mg" refers to milligrams; "mmol" refers to millimoles; "mL" refers to milliliters; "bp" refers to boiling point; "mp" refers to melting point; "° C." refers to degrees Celsius; "mm Hg" refers to millimeters of mercury; "μL" refers to microliters; "μg" refers to micrograms; and "μM" refers to micromolar.

EXAMPLE 1

1-(1-Oxopentyl-5-isopentylsulfide)-4-hydroxypiperidine

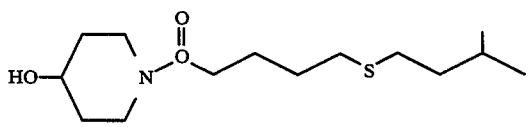

Step a:
1-(1-Oxopentyl-5-chloro)-4-(O-tert-butyldimethylsilyloxy)piperidine

Mix 4-hydroxypiperidine (1.14g, 11.3 mmol), dimethylaminopyridine (0.1g), triethylamine (5 mL, 36 mmol) and methylene chloride (25 mL). Place under a nitrogen and cool to 0° C. Add, by dropwise addition, a solution of tertbutyldimethylsilyl chloride (3.57g, 24 mmol) in methylene chloride (50 mL). Allow to warm to room temperature and stir for 7 hours. Quench with methanol and stir overnight. Evaporate the solvent in vacuo and take up the residue in water. Extract with ethyl ether, dry (MgSO$_4$) and evaporate the solvent in vacuo to give 4-(O-tert-butyldimethylsilyl)piperidine (629 mg, 26%) as a yellow oil. 332E-184

Dissolve 4-(O-tert-butyldimethylsilyl)-piperidine (470 mg, 2.18 mmol) and triethylamine (1.52 mL, 10.9 mmol) in methylene chloride (25 mL). Place under a nitrogen atmosphere and cool to 0° C. Add, by dropwise addition, a solution of 5-chloro pentanoylchloride (282 μg, 2.18 mmol) in methylene chloride (10 mL). Allow to warm to room temperature and stir for 2 hours. Pour into ice water, extract into methylene chloride, dry (MgSO$_4$) and evaporate the solvent in vacuo to give 790 mg crude product. Purify by flash chromatography (20% ethyl acetate/hexane followed by 40% ethyl acetate/hexane) to give the title compound (690 mg, 95%). 332E-169 MDL 44,782

Anal. Calcd for C$_{16}$H$_{32}$ClNO$_2$Si: C, 57.54; H, 9.66, N, 4.19;

Found: C, 57.47, H, 9.73, N, 4.24.

Step b:
1-(1-Oxopentyl-5-isopentylsulfide)-4-hydroxypiperidine

Prepare sodium ethoxide by dissolving sodium metal (0.14g, 6 mmol) in absolute ethanol (5 mL). Place under a nitrogen atmosphere and add 3-methyl-l-butanethiol (0.75 mL, 6 mmol) and stir at room temperature for 1 hour. Add a solution of 1-(1-oxopentyl-5-chloro)-4-(O-tert-butyl-dimethylsilyloxy)piperidine (2.0g, 6 mmol) in ethanol (5 mL). and heat at reflux overnight. Cool to room temperature and partition between methylene chloride (100 mL) and 10% sodium hydroxide (100 mL). Separate the organic phase, wash with 10% sodium hydroxide (50 mL), water and brine. Dry (Na$_2$SO$_4$) and evaporate the solvent in vacuo. Purify by flash chromatography (70% hexane/ethyl acetate) to give 1-(1-oxopentyl-5-isopentylsulfide)-4-(O-tert-butyl-dimethylsilyloxy)-piperidine Dissolve 1-(1-oxopentyl-5-isopentylsulfide)-4-(O-tert-butyldimethylsilyloxy)piperidine (201 mg, 0.5 mmol) in a mixture of acetic acid, tetrahydrofuran, and water in a 3:2:2 ratio. Stir at 70° C. for 3 days, cool to room temperature and add ether (100 mL). Separate the organic phase, wash with 10% sodium hydroxide (25 mL) and dry (MgSO$_4$). Evaporate the solvent in vacuo to give 129 mg of crude product. Purify by flash chromatography to give the title compound.

EXAMPLE 2

1-(1-Oxopentyl-5-isopentylsulfide)-4-[(2-hydroxy-1-methyl)ethylpiperidine

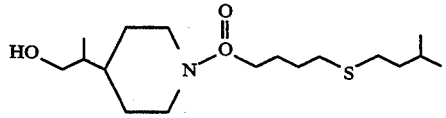

Step a: 1-(1-Oxopentyl-5-chloro)-4-[(2-t-butyldimethylsiloxy-1-methyl)ethyl]piperidine Dissolve triethyl 2-phosphonopropionate (5.72g, 24 mmol) in anhydrous tetrahydrofuran (250 mL), cool to −78° C. and place under argon atmosphere. Add a solution of n-butyllithium in hexane (16.3 mL, 26 mmol). Stir at −78° C. for 10 minutes, then add, by dropwise addition, a solution of N-benzyl-4-piperidinone (3.79g, 20 mmol) in tetrahydrofuran (50 mL). Stir for 10 minutes, allow to warm to room temperature, and stir for an additional 17 hours. Dilute with saturated ammonium chloride (100 mL), wash twice with 10% sodium hydroxide and dry (MgSO$_4$). Evaporate the solvent in vacuo to yield 6.58 g. Purify by silica gel chromatography (25% ethyl acetate/hexane) to yield 5.25 g (96%) of 2-[1-(phenylmethyl)-4-piperidylinylidene]propanoic acid, ethyl ester as a colorless oil; MS (CI/CH$_4$) m/z 274 (M+1), 228 (M+1-EtOH), 196 (M+H−C$_6$H$_6$).

Dissolve 2-[1-(phenylmethyl)-4-piperidinylidene]-propanoic acid, ethyl ester (18.44 gg, 67.45 mmol) in anhydrous ethyl ether (200 mL). Place under a nitrogen atmosphere and cool to 0°–5° C. Slowly add a solution of lithium aluminum hydride (77 mL of a 1.0M solution in ether, 77 mmol) and stir for 15 minutes. Carefully add water (3.0 mL), then 10% sodium hydroxide (3 mL) then water (9 mL). Stir at room temperature for 3 hours, filter and evaporate the solvent in vacuo to give 1-phenylmethyl-4-[(2-hydroxy-1-methyl)ethyl]piperidinylidene (15.35 g, 98%).

Dissolve 1-phenylmethyl-4-[(2-hydroxy-1-methyl)ethyl]piperidinylidene (15.35 g, 66.35 mmol) in methylene chloride (250 mL),place under a nitrogen atmosphere and add dimethylaminopyridine (100 mL) and triethylamine (10.5 mL, 75 mmol). Add tert-butyl-dimethylsilylchloride (11.0 g, 73 mmol) and stir at room temperature overnight. Wash with 10% sodium hydroxide, separate the organic phase, dry (MgSO$_4$) and evaporate the solvent in vacuo. Purify by chromatography (20% ethyl acetate/hexane) to give 1-phenylmethyl-4-[(2-t-butyl-dimethylsiloxy-1methyl)ethyl]piperidinylidene (22.27 g).

Dissolve 1-phenylmethyl-4-[(2-t-butyl-dimethylsiloxy-1-methyl)ethyl]piperidinylidene (1.5g, 4.34 mmol) in 9A ethanol (50 mL) and place in a Paar hydrogenation flask. Add 20% Pd(OH)$_2$/carbon (300 mg). Charge the vessel to 50psi and shake for 17.5 hours. Filter the solution through filter aid and remove the solvent in vacuo to give 4-[(2-t-butyl-dimethylsiloxy-1-methyl)ethyl]piperidine.

Dissolve 4-[(2-t-butyl-dimethylsiloxy-1-methyl)ethyl]piperidine (1.36g, 5.3 mmol) and triethylamine (3 mL) in methylene chloride (50 mL). Place under a nitrogen atmosphere and cool to 0° C. Add a solution of 5-chlorovaleryl chloride (0.68 mL, 5.3 mmol) in methylene chloride (15 mL). Warm to room temperature and stir for 4 hours. Dilute with methylene chloride (100 mL) and wash with 10 % sodium hydroxide. Dry (MgSO$_4$) and evaporate the solvent in vacuo to give a golden oil. Purify by flash chromatography (30% ethyl acetate/hexane ) to give the title compound (1.82 g, 91% ) .

Anal. Calcd for C$_{19}$H$_{38}$ClNO$_2$Si: C, 60.68; H, 10.19, N, 3.72;
Found: C, 60.50; H, 10.34; N, 3.92.

Step b :
1-(1-Oxopentyl-5-isopentylsulfide)-4-[(2-hydroxy-1-methyl )ethyl]piperidine Mix 1- (1-oxopentyl-5-chloro)-4-[(2-t-butyl-dimethylsiloxy-1-methyl)ethyl]piperidine (376 mg, 1 mmol), potassium carbonate (165 mg ) and dimethylformamide (10 mL). Add 3-methylbutanethiol (150μl, 1.2 mmol). Warm to 40°–60° C. for 3 days, adding additional potassium carbonate and 3-methylbutanethiol on the 2nd day. Pour into water, dilute with ether and wash with water. Dry (MgSO$_4$), evaporate the solvent in vacuo and purify by chromatography (70:30 hexane/ethyl acetate) to give 1-(1-oxopentyl-5-isopentylsulfide)-4-[(2-t-butyl-dimethylsiloxy-1-methyl) ethyl]piperidine (311 mg).

Dissolve 1-(1-oxopentyl-5-isopentylsulfide)-4-[(2-t-butyl-dimethylsiloxy-1-methyl)ethyl]piperidine (311 mg) in a mixture of acetic acid, tetrahydrofuran, and water in a 3:2:2 ratio.
Stir at 80° C. for 24 hours, cool to room temperature and add ether. Wash with 10% sodium hydroxide, dry (MgSO$_4$) and evaporate the solvent in vacuo. Dissolve the residue in methanol and treat with 1.0M lithium hydroxide. Stir for 10 minutes at room temperature, dilute with ether, wash with water and dry (MgSO$_4$). Evaporate the solvent in vacuo to give the title compound (197 mg).

Anal. Calcd for C$_{18}$H$_{35}$NO$_2$S: C, 65.60; H, 10.71, N, 4.25;
Found: C, 65.67; H, 10.69; N, 4.35.

EXAMPLE 3

1-(1-Oxopentyl-5-phenylsulfide)-4-[(2-hydroxy-1-methyl)ethyl]piperidine

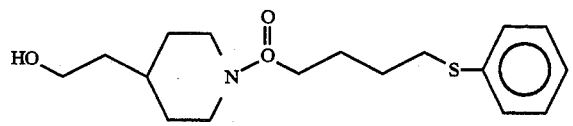

Mix 1-(1-oxopentyl-5-chloro)-4-[(2-t-butyl-dimethylsiloxy-1-methyl)ethyl]piperidine (485 mg), potassium carbonate (large excess) and dimethylformamide (10 mL). Add 3-methylbutanethiol (large excess). Warm to 60° C. overnight, pour into water, dilute with ether and wash with water. Dry (MgSO$_4$), evaporate the solvent in vacuo and purify by chromatography (70:30 hexane/ethyl acetate) to give 1-(1-oxopentyl-5-phenylsulfide)-4-[(2-t-butyl-dimethylsiloxy-1-methyl)ethyl]piperidine (433 mg).

Dissolve 1-(1-oxopentyl-5-phenylsulfide)-4-[(2-t-butyl-dimethylsiloxy-1-methyl) ethyl]piperidine (433 mg) in a mixture of acetic acid, tetrahydrofuran, and water in a 3:2:2 ratio. Stir at 90°–100° C. for 24 hours, cool to room temperature and add ether. Wash with 10% sodium hydroxide, dry (MgSO$_4$) and evaporate the solvent in vacuo. Dissolve the residue in methanol and treat with 1.0M lithium hydroxide. Stir for 10 minutes at room temperature, dilute with ether, wash with water and dry (MgSO$_4$). Evaporate the solvent in vacuo and purify by chromatography (3:1 ethyl acetate/hexae) to give the title compound (264 mg).

Anal. Calcd for C$_{19}$H$_{29}$NO$_2$S: C, 68.02; H, 8.71, N, 4.17;

Found: C, 67.77; H, 8.95; N, 3.95.

The following compounds can be prepared by procedures analogous to those described above in Examples 1–3:

1-(1-Oxopentyl-5-cyclohexylsulfide)-4-[(2-hydroxy-1-methyl)ethyl]piperidine;
1-(1-Oxopentyl-5-phenylmethylsulfide)-4-[(2-hydroxy-1-methyl)ethyl]piperidine;
1-(1-Oxopentyl-5-(2-furanylmethylsulfide)-4-[(2-hydroxy-1-methyl)ethyl]piperidine;
1-(1-Oxopentyl-5-(2-thiophenylmethylsulfide)-4-[(2-hydroxy-1-methyl)ethyl]piperidine and
1-(1-Oxopentyl-5-isopentylsulfide)piperidine.

The compounds of Formula (I) wherein Y is methylene can be prepared by utilizing procedures and techniques well known and appreciated in the art. A general synthetic scheme for preparing these compounds is set forth in Scheme B wherein all substituents, unless otherwise indicated, are as previously defined.

Scheme B

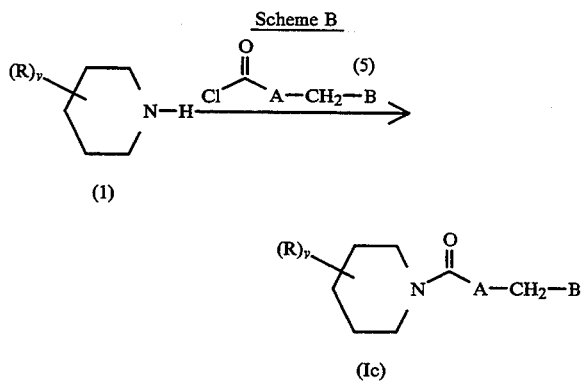

Scheme B provides a general synthetic scheme for preparing compounds of Formula (I) wherein Y is a methylene. The compound of Formula (Ic) can be prepared by reacting the appropriate piperidine compound of structure (1) with an appropriate acid chloride of structure (5) as described previously in Scheme A, step a.

Starting materials for use in the general synthetic procedures outlined in Scheme B are readily available to one of ordinary skill in the art.

The following examples present typical syntheses as described in Scheme B. These examples are understood to be illustrative only and are not intended to limit the scope of the present invention in any way.

EXAMPLE 4

1-Oxododecyl-4-hydroxypiperidine

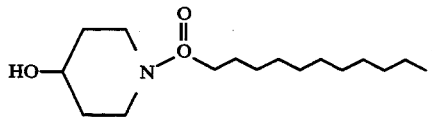

Dissolve lauric acid (0.77 g) in methylene chloride (50 mL) and cool to 0° C. Add oxalyl chloride (0.37 mL) and dimethylformamide (3 drops). Allow to warm to room temperature and stir for 1 hour. Add this solution to a mixture of 4-(O-tert-butyldimethylsilyloxy)-piperidine and triethylamine (1 mL) in methylene chloride (25 mL). Heat at reflux overnight. Dilute with methylene chloride (50 mL) and separate the organic phase. Wash twice with 10% sodium hydroxide, once with water, and once with brine. Dry (Na$_2$SO$_4$) and evaporate the solvent in vacuo. Dissolve the residue in hexane (100 mL) and wash twice with 10% hydrochloric acid (50 mL), once with saturated sodium hydrogen carbonate and once with brine. Dry (Na2SO4) and evaporate the solvent in vacuo to give 1-oxododecyl-4-(O-tertbutyldimethylsilyloxy)piperidine.

Mix 1-oxododecyl-4-(O-tert-butyldimethylsilyloxy)-piperidine (3.5 mmol) with a solution of acetic acid (9 mL), tetrahydrofuran (6 mL) and water (6 mL). Heat at 75° C overnight. Cool to room temperature and make basic with 10% sodium hydroxide and extract into methylene chloride. Wash with water, then with brine and dry (Na2SO4). Evaporate the solvent in vacuo and purify by flash chromatography (5% methanol/methylene chloride) to give the title compound. 587E-115

Anal. Calcd for C$_{17}$H$_{33}$NO$_2$: C, 72.03; H, 11.73; N, 4.94; Found: C, 72.47; H, 11.62; N, 4.90.

EXAMPLE 5

1-Oxododecyl-3-hydroxypiperidine

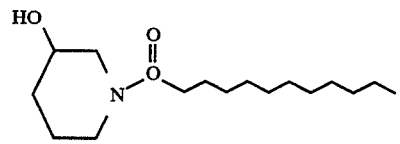

Mix 3-hydroxypiperidine (1.14 g, 11.3 mmol), dimethylaminopyridine (0.1 g), triethylamine (5 mL, 36 mmol) and methylene chloride (25 mL). Place under a nitrogen and cool to 0° C. Add, by dropwise addition, a solution of tertbutyldimethylsilyl chloride (3.57 g, 24 mmol) in methylene chloride (50 mL). Allow to warm to room temperature and stir for 7 hours. Quench with methanol and stir overnight. Evaporate the solvent in vacuo and take up the residue in water. Extract with ethyl ether, dry (MgSO$_4$) and evaporate the solvent in vacuo to give 3-(O-tert-butyldimethylsilyl)piperidine.

Dissolve lauric acid (0.77 g) in methylene chloride (50 mL) and cool to 0° C. Add oxalyl chloride (0.37 mL) and dimethylformamide (3 drops). Allow to warm to room temperature and stir for 1 hour. Add, by dropwise addition, to a solution of 3-(O-tert-butyldimethylsilyloxy)piperidine (0.76 g, 3.5 mmol) and triethylamine (1 mL) in methylene chloride (20 mL). Stir overnight. Dilute with methylene chloride (50 mL) and separate the organic phase. Wash twice with 10% sodium hydroxide, once with 10% hydrochloric acid, and once with saturated sodium hydrogen carbonate and once with brine. Dry (Na2SO4) and evaporate the solvent in vacuo to give 1-oxododecyl-3-(O-tert-butyldimethylsilyloxy)piperidine.

Mix 1-oxododecyl-3-(O-tert-butyldimethylsilyloxy)-piperidine (3.5 mmol) with a solution of acetic acid (9 mL), tetrahydrofuran (6 mL) and water (6 mL). Heat at 75° C. overnight. Cool to room temperature and make basic with cold 10% sodium hydroxide and extract into methylene chloride. Wash with water, then with brine and dry (Na$_2$SO$_4$). Evaporate the solvent in vacuo and purify by flash chromatography (5% methanol/methylene chloride) to give the title compound.

The compounds of Formula (II) can be prepared by utilizing procedures and techniques well known and appreciated in the art. A general synthetic scheme for preparing these compounds is set forth in Scheme F wherein all substituents, unless otherwise indicated, are as previously defined.

Scheme F

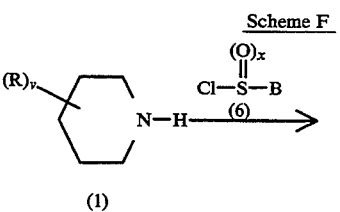

-continued
Scheme F

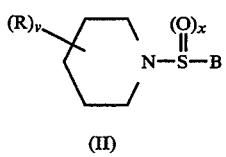

(II)

Scheme F provides a general synthetic scheme for preparing compounds of Formula (II). The appropriate piperidinyl sulfonamide of Formula (II) can be prepared by an amidation reaction of the piperidine compound of structure (1) with an appropriate sulfonyl chloride or sulfoxyl chloride of structure (6) as described previously in Scheme A, step a. For those piperidinyl sulfonamides and sulfoxamides of formula (II) wherein R is $-(CH_2)_m OH$ or a radical of the formula $-CH(R_1)-(CH_2)_n-CH_2OH$, the starting piperidine compound of structure (1) is one wherein R is represented by $-CO_2C_1-C_4$ alkyl or a radical of the formula $-CH(R_1)-(CH_2)_n-CO_2C_1-C_4$ alkyl. The ester functionality of the resulting piperidinyl sulfonamides and sulfoxamides of formula (II) wherein R is $-CO_2C_1-C_4$ alkyl or a radical of the formula $-CH(R_1)-(CH_2)n-CO_2C_1-C_4$ alkyl is then reduced by techniques and procedures well known and appreciated by one of ordinary skill in the art to give the corresponding piperidinyl sulfonamides and sulfoxamides of formula (II) wherein R is $-(CH_2)_m OH$ or a radical of the formula $-CH(R_1)-(CH_2)_n-CH_2OH$.

Starting materials for use in the general synthetic procedures outlined in Scheme F are readily available to one of ordinary skill in the art.

The following examples present typical syntheses as described in Scheme F. These examples are understood to be illustrative only and are not intended to limit the scope of the present invention in any way.

EXAMPLE 6

1-(1-Sulfoxododecyl)-4-[(2-hydroxy-1-methyl)ethyl]-piperidine

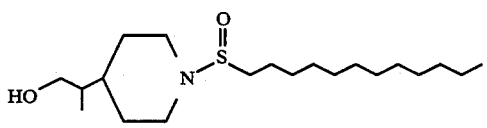

Dissolve 2-[1-(phenylmethyl)-4-piperidinylidene]-propanoic acid, ethyl ester (5.5 g, 20 mmol) in acetic acid (75 mL) and place in a Paar hydrogenation flask. Add 20% Pd(OH)$_2$/carbon (550 mg). Charge the vessel to 50psi and shake for 24 hours. Filter the solution through filter aid and remove the solvent in vacuo. Dissolve the residue in ether and water. Add solid potassium carbonate until the pH is strongly basic. Dilute with ether, extract into ether (2X), dry (MgSO$_4$) and evaporate the solvent in vacuo to give 2-[4-piperidine]propanoic acid, ethyl ester.

Dissolve 2-[4-piperidine]propanoic acid, ethyl ester (480 mg) and triethylamine (0.3–0.5 mL) in methylene chloride. Place under a nitrogen atmosphere and cool to 0° C. Add a solution of 1-dodecane sulfoxyl chloride (652 mg, 2.6 mmol). Warm to room temperature and stir for 3 hours. Dilute with methylene chloride (100 mL) and wash with 10% sodium hydroxide. Dry (MgSO$_4$) and evaporate the solvent in vacuo to give a yellow oil. Purify by flash chromatography (50% ethyl acetate/hexane) to give 1-(1-sulfoxododecyl)-2-[4-piperidine]propanoic acid, ethyl ester (804 mg, 48%).

Dissolve 1-(1-sulfoxododecyl)-2-[4-piperidine]-propanoic acid, ethyl ester (2.0 mmol) in tetrahydrofuran (20 ml), place under a nitrogen atmosphere and cool to −78° C. Add DIBAL-H (8.0 mmol of a 1M solution in hexane). Stir at room temperature overnight. Filter through filter aid and evaporate the solvent in vacuo. Purify by chromatography to give the title compound.

Anal. Calcd for C$_{20}$H$_{41}$NO$_2$S: C, 66.80; H, 11.49; N, 3.89;

Found: C, 66.81; H, 11.55; N, 3.91.

EXAMPLE 7

1-(1-Sulfonododecyl)-4-[(2-hydroxy-1-methyl)ethyl)-]piperidine

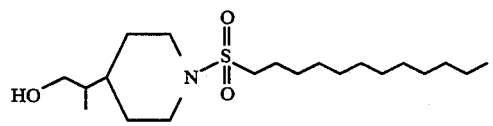

Dissolve 2-[4-piperidine]propanoic acid, ethyl ester (934 mg, 5.04 mmol) and triethylamine (2 mL) in methylene chloride (25 mL). Add 1-dodecane sulfonyl chloride (1.36 g, 5.04 mmol). Stir overnight at room temperature under a nitrogen atmosphere. Evaporate the solvent in vacuo, dissolve in 10% sodium hydroxide and extract into ether. Dry (MgSO$_4$) and evaporate the solvent in vacuo to give a white solid. Purify by flash chromatography (25% ethyl acetate/hexane) to give 1-(1-sulfonododecyl)-2-[4-piperidine]propanoic acid, ethyl ester (1.38 mg, 66%).

Dissolve 1-(1-sulfonododecyl)-2-[4-piperidine]-propanoic acid, ethyl ester (376 mg, 0.90 mmol) in ether (50 ml), place under a nitrogen atmosphere and cool to 0°–5° C. Add lithium aluminum hydride (1.0 mL of a 1M solution in hexane, 1.0 mmol). Stir at room temperature for 3 hours. Add water (50 μL), 10% sodium hydroxide (50 μL) then water (150 μL). Dry (MgSO$_4$) and evaporate the solvent in vacuo to give the title compound.

EXAMPLE 8

1-(1-Sulfonododecyl)-4-[(2-hydroxy)ethyl]piperdine

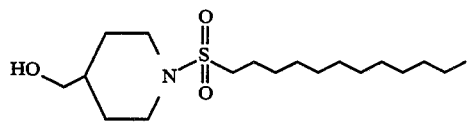

Dissolve 4-piperidinecarboxylic acid acid, ethyl ester hydrochloride (450 mg, 2.5 mmol) in methylene chloride (2 mL). Add 1-dodecane sulfonyl chloride (672 mg, 2.5 mmol). Dilute to almost 10 mL with methylene chloride. Add triethylamine (excess) and stir at room temperature under a nitrogen atmosphere for 4 hours. Dilute with methylene chloride (100 mL), wash with 10% sodium hydroxide, dry (MgSO$_4$) and evaporate the solvent in vacuo. Purify by flash chromatography (50% ethyl acetate/hexane) to give 1-(1-sulfonododecyl)-[4-piperidine]carboxylic acid, ethyl ester (743 mg).

Dissolve 1-(1-sulfonododecyl)-[4-piperidine]carboxylic acid, ethyl ester (743 mg, 1.98 mmol) in tetrahydrofuran (10 ml), place under a nitrogen atmosphere and cool to 0°-5° C. Add lithium aluminum hydride (2.0 mL of a 1M solution in hexane, 2.0 mmol). Stir at room temperature for 3 hours. Add water (75 µL), 10% sodium hydroxide (75 µL) then water (225 µL) and stir overnight. Dilute with ether, dry (MgSO$_4$) and evaporate the solvent in vacuo to give the title compound; mp 73.2°-74.8° C.

Anal. Calcd for $C_{18}H_{37}NO_3S$: C, 62.21; H, 10.73; N, 4.03;

Found: C, 62.35; H, 10.99; N, 4.26.

The following examples illustrate the utility of compounds of formula (I) and formula (II) in inhibiting cholesterol biosynthesis. These examples are understood to be illustrative only and are not intended to limit the scope of the present invention in any way.

EXAMPLE 9

Inhibition of Cholesterol Biosynthesis

Microsomes, prepared by ultracentrifugation of homogenates of rat liver, are incubated at 37° C. for 45 minutes in the presence of 60 µM $^3$H-squalene, 2.0 mM NADPH, 0.01 mM FAD, and the high speed supernatant fraction from the microsomal preparation. Blanks, in which NADPH has been omitted, are run simultaneously with the test compounds. Compounds are tested at concentrations of 0.0 to 100.0 µM.

a) TLC Assay: Following incubation, the samples are saponified, standards are added to each sample, and then the reaction products are extracted into hexane. The hexane extracts are dried and then the dried extracts are redissolved in chloroform. The reaction products (3S)-2,3-oxidosqualene and lanosterol contained in the extracts are then separated by TLC. Spots containing the reaction products are scraped from the TLC plates and counted for $^3$H-radioactivity in a scintillation counter. An IC$_{50}$ for squalene epoxidase and oxidosqualene cyclase is calculated.

b) HPLC Assay

Following incubation, reactions are stopped by the addition of chloroform:methanol, standards are added, then reaction products and standards are extracted into chloroform. The chloroform extracts are dried, and the residue is dissolved in toluene:methanol. The reaction products and standards contained in the dissolved residue are separated by high performance liquid chromatography (HPLC). Chromatographic peaks containing reaction products are monitored for $^3$H-radioactivity with a flow-through scintillation counter connected in series with the HPLC column. An IC$_{50}$ is calculated for squalene epoxidase and oxidosqualene cyclase based on the radioactivity in controls and samples.

EXAMPLE 10

Inhibition of Purified Oxidosqualene Cycloase (I$_{10}$)

Oxidosqualene cyclase is purified from rat liver microsomes by the sequential methods of: 1) solublization with the detergent lauryl maltoside and 2) FPLC anion-exchange chromatography. Compounds are tested to determine their ability to inhibit the conversion of squalene monoepoxide to lanosterol catalyzed by the purified oxidosqualene cyclase. The reaction mixture (final volume, 200 µL), contains potassium phosphate buffer (50mM, pH 7.4), Na$_2$EDTA (500 µM), Tween (80 (0.1%), [$^3$H]squalene monoepoxide (10 µM of the racemic mixture, 50Ci/mol), test compound (10 µM) and purified oxidosqualene cyclase (50 µg). The reagents, prior to mixing are equilibrated at 37° C. for 10 minutes. The reaction is initiated by adding enzyme. The reaction is terminated by the addition of 5 mL of CHCl$_3$/MeOH (2:1, v/v), 0.8 mL of water and 10 µg each of squalene monoepoxide, squalene diepoxide, lanosterol and cholesterol. The organic layer is isolated and evaporated to dryness under nitrogen. The residue is dissolved in 200 µL of hexane/ethanol (99:1) and the sample is subjected to HPLC separation using a C$_{18}$ reverse phase column eluted isocratically with 3.6% water in methanol. Radioactivity is quantitated using an in-line scintillation counter. Oxidosqualene cyclase activity is expressed as the percent inhibition of oxidosqualene cyclase activity at 10 µM test compound (I$_{10}$ values).

Table 1 provides a summary of the testing data for the inhibition of oxidosqualene cyclase by compounds of formula (I) and formula (II).

TABLE 1

| Inhibition of Oxidosqualene Cyclase | |
|---|---|
| Compound | % Inhibition @ 10 µM [I$_{10}$] |
| 101,550 | 82 |
| 100,759 | 76 |
| 101,915 | 46 |
| 102,055 | 29 |
| 101,140 | 38 |

101,550 = 1-(1-Oxopentyl-5-phenylsulfide)-4-[(2-hydroxy-1-methyl)ethyl]piperidine 100,759 = 1-(1-Oxopentyl-5-isopentylsulfide)-4-[(2-hydroxy-1-methyl)ethyl]piperidine 101,915 = 1-(1-Sulfoxododecyl)-4-[(2-hydroxy-1-methyl)ethyl]piperdine 102,055 = 1-(1-Sulfonododecyl)-4-[(2-hydroxy-1-methyl)ethyl]piperdine 101,140 = 1-(1-Oxopentyl-5-isopentylsulfide)piperdine In a further embodiment, the present invention provides a method of inhibiting cholesterol biosynthesis in a patient in need thereof comprising administering to said patient an effective cholesterol biosynthesis inhibitory amount of a compound of formula (I) and formula (II). The present invention also provides a method of lowering plasma cholesterol in a patient in need thereof, and a method of treating a patient afflicted with hypercholesterolemia, comprising administering to said patient an effective hypocholesterolemic amount of a compound of formula (I) or formula (II).

It is believed that the compounds of the present invention exert their inhibitory effect on cholesterol biosynthesis through inhibition of squalene epoxidase and/or oxidosqualene cyclase. However, the present invention is not intended to be limited to a particular mechanism of action in achieving inhibition of cholesterol biosynthesis in a patient in need thereof.

As used herein, the term "patient" refers to warm-blooded animals or mammals, including humans. A patient is in need of treatment to inhibit cholesterol biosynthesis or to reduce plasma cholesterol when the patient is suffering from hypercholesterolemia, such as, for example, in the case of a patient suffering from familial hyperlipidemia.

Hypercholesterolemia is a disease state characterized by levels of plasma cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

An effective hypocholesterolemic amount of a compound of formula (I) or formula (II) is an amount which is effective in reducing plasma cholesterol levels or LDL cholesterol levels in a patient in need thereof. As such, successful treatment of a patient for hypercholesterolemia is understood to include reducing a patient's plasma cholesterol or LDL cholesterol levels. Successful treatment for hypercholesterolemia is also understood to include prophylaxis in preventing clinically significant elevations in plasma cholesterol or in LDL cholesterol levels in a patient who is at risk of the development of hypercholesterolemia.

An effective cholesterol biosynthesis inhibitory amount of a compound of formula (I) or formula (II) is an amount which is effective in inhibiting cholesterol biosynthesis in a patient in need thereof which results in the lowering of plasma cholesterol levels or LDL cholesterol levels.

An effective hypocholesterolemic dose or an effective cholesterol biosynthesis inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective hypocholesterolemic amount, and an effective cholesterol biosynthesis inhibitory amount, of a compound of formula (I) or formula (II) will generally vary from about 0.1 milligram per kilogram of body weight per day (mg/kg/day) to about 500 mg/kg/day. A daily dose of from about 0.3 mg/kg to about 80 mg/kg is preferred.

In effecting treatment of a patient, compounds of formula (I) or formula (II) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the disease state to be treated, the stage of the disease, and other relevant circumstances.

Compounds of formula (I) or formula (II) can be administered in the form of pharmaceutical compositions or medicaments which are made by combining the compounds of formula (I) or formula (II) with pharmaceutically acceptable carriers or excipients, the proportion and nature of which are determined by the chosen route of administration, and standard pharmaceutical practice.

In another embodiment, the present invention provides compositions comprising a compound of formula (I) or formula (II) in admixture or otherwise in association with one or more inert carriers. These compositions are useful, for example, as assay standards, as convenient means of making bulk shipments, or as pharmaceutical compositions. An assayable amount of a compound of formula (I) or formula (II) is an amount which is readily measurable by standard assay procedures and techniques as are well known and appreciated by those skilled in the art. Assayable amounts of a compound of formula (I) or formula (II) will generally vary from about 0,001% to about 75% of the composition by weight. Inert carriers can be any material which does not degrade or otherwise covalently react with a compound of formula (I) or formula (II). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of formula (I) or formula (II) in admixture or otherwise in association with one or more pharmaceutically acceptable carriers or excipients.

The pharmaceutical compositions or medicaments are prepared in a manner well known in the pharmaceutical art. The carrier or excipient may be a solid, semisolid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of formula (I) or formula (II) may be incorporated with excipients and used in the form of tablets, troches, capsules, elixirs, suspensions, syrups, wafers, chewing gums and the like. These preparations should contain at least 4% of the compound of formula (I) or formula (II), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of formula (I) or formula (II) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of formula (I) or formula (II) in their end-use application.

The following specific compounds of formula (I) and formula (II) are particularly preferred in the end-use application of the compounds of the present invention:

1-(1-Oxopentyl-5-phenylsulfide)-4-[(2-hydroxy-1-methyl)ethyl]piperidine;

1-(1-Sulfonododecyl)-4-[(2-hydroxy-1-methyl)ethyl]-piperidine and 1-(1-Oxopentyl-5-isopentylsulfide)piperidine.

What is claimed is:

1. A compound of the formula

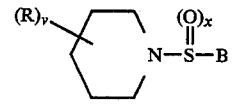

wherein B is a $C_5$–$C_{14}$ alkyl,

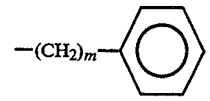

or

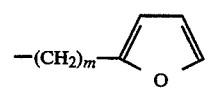

m is an integer 0 or 1;
x is an integer 1 or 2;
v is an integer 0, 1 or 2; and
R is -$(CH_2)_m$OH, with the proviso that when m is 0, R cannot be in the 2-position of the piperidine ring or a radical of the formula

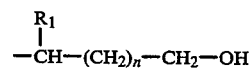

wherein n is an integer 0, 1, 2 or 3; and $R_1$ is hydrogen, phenyl, vinyl or a $C_1$–$C_4$ alkyl.

2. A method of inhibiting the biosynthesis of cholesterol in a patient in need thereof comprising administering to said patient an effective cholesterol biosynthesis inhibiting amount of a compound of claim 1.

3. A method of lowering plasma cholesterol in a patient in need thereof comprising administering to said patient an effective hypocholesterolemic amount of a compound of claim 1.

4. A method of treating a patient afflicted with hypercholesterolemia comprising administering to said patient an effective hypocholesterolemic amount of a compound of claim 1.

5. A pharmaceutical composition comprising an effective hypocholesterolemic amount of a compound of claim 1 in admixture or otherwise in association with one or more pharmaceutically acceptable carriers or excipients.

6. A compound of claim 1 wherein the compound is 1-(1-Sulfonododecyl)-4-piperidine.

7. A compound of claim 1 wherein the compound is 1-(1-Sulfonododecyl)-4-piperidine.

* * * * *

UNITED STATES PATENT AND TRADEMARK OFFICE
CERTIFICATE OF CORRECTION

PATENT NO. : 5,350,758  Page 1 of 2

DATED : Sep. 27, 1994

INVENTOR(S) : Marion W. Wannamaker, William A. VanSickle, William R. Moore

It is certified that error appears in the above-identified patent and that said Letters Patent is hereby corrected as shown below:

Column 2, Line 25 patent reads " $\overset{O}{\underset{O}{\parallel}}$ " and should read -- $\overset{O}{\underset{C}{\parallel}}$ --.

Column 5, Line 40 patent reads " $\overset{O}{\underset{O}{\parallel}}$ " and should read -- $\overset{O}{\underset{C}{\parallel}}$ --.

Column 6, Line 45 patent reads " $\overset{O}{\underset{O}{\parallel}}$ " and should read -- $\overset{O}{\underset{C}{\parallel}}$ --.

Column 8, Line 18 patent reads " $\overset{O}{\underset{O}{\parallel}}$ " and should read -- $\overset{O}{\underset{C}{\parallel}}$ --.

Column 9, Line 35 patent reads " $\overset{O}{\underset{O}{\parallel}}$ " and should read -- $\overset{O}{\underset{C}{\parallel}}$ --.

Column 10, Line 7 patent reads " $\overset{O}{\underset{O}{\parallel}}$ " and should read -- $\overset{O}{\underset{C}{\parallel}}$ --.

UNITED STATES PATENT AND TRADEMARK OFFICE
CERTIFICATE OF CORRECTION

PATENT NO. : 5,350,758

DATED : Sep. 27, 1994

INVENTOR(S) : Marion W. Wannamaker, William A. VanSickle, William R. Moore

It is certified that error appears in the above-identified patent and that said Letters Patent is hereby corrected as shown below:

Column 3, Line 39 patent reads: "$-C(CH_3)-CH_2-$" and should read -- $-CH(CH_3)-CH_2-$ --.

Column 4, Line 61 patent reads: "by one or ordinary skill" and should read --.

Column 9, Line 55 patent reads: "$(Na_2SO4)$" and should read -- $(Na_2SO_4)$ --.

Column 9, Line 65 patent reads: "$(Na_2SO4)$" and should read -- $(Na_2SO_4)$ --.

Column 10, Line 39 patent reads: "$(Na_2SO4)$" and should read -- $(Na_2SO_4)$ --. Column 12, Line 57 patent reads: "acid acid" and should read -- acid --.

Column 16, Line 23 patent reads: "0,001%" and should read -- 0.001% --.

Signed and Sealed this

Fifth Day of September, 1995

Attest:

BRUCE LEHMAN

Attesting Officer

Commissioner of Patents and Trademarks